(12) United States Patent
Meyer

(10) Patent No.: US 6,379,916 B1
(45) Date of Patent: Apr. 30, 2002

(54) DEVICE AND PROCESS FOR THE EXAMINATION OF CELLS USING THE PATCH-CLAMP METHOD

(75) Inventor: Joerg Uwe Meyer, St. Ingbert (DE)

(73) Assignee: Fraunhofer-Gesellschaft zur Forderung der Angwandten Forschung e.V., Munich (DE)

( * ) Notice: Subject to any disclaimer, the term of this patent is extended or adjusted under 35 U.S.C. 154(b) by 0 days.

(21) Appl. No.: 09/529,162

(22) PCT Filed: Oct. 9, 1998

(86) PCT No.: PCT/EP98/06418

§ 371 Date: May 30, 2000

§ 102(e) Date: May 30, 2000

(87) PCT Pub. No.: WO99/19729

PCT Pub. Date: Apr. 22, 1999

(30) Foreign Application Priority Data

Oct. 9, 1997 (DE) .......................................... 197 44 649

(51) Int. Cl.⁷ .............................. C12Q 1/02; C12Q 1/00

(52) U.S. Cl. ........................... 435/29; 435/4; 435/283.1; 435/287.1; 435/288.4

(58) Field of Search ........................... 435/29, 4, 283.1, 435/287.1, 288.4

(56) References Cited

U.S. PATENT DOCUMENTS 6,063,260 A * 5/2000 Olesen et al. ................ 205/793

FOREIGN PATENT DOCUMENTS

WO 96-13721 * 5/1996

* cited by examiner

*Primary Examiner*—Louise N. Leary
(74) *Attorney, Agent, or Firm*—Antonelli, Terry, Stout & Kraus, LLP

(57) ABSTRACT

Disclosed is a device and a process for examining cells using the patch-clamp method. A plane arrangement is used of a first number of micro-cuvettes for receiving cells and a plane arrangement of a second number of micro-pipettes which can be positioned in relation to the plane arrangement of micro-cuvettes in such a manner that a multiplicity of cells located in the micro-curvettes can be examined simultaneously.

35 Claims, 2 Drawing Sheets

DEVICE AND PROCESS FOR THE EXAMINATION OF CELLS USING THE PATCH-CLAMP METHOD

TECHNICAL FIELD

Figure 1:
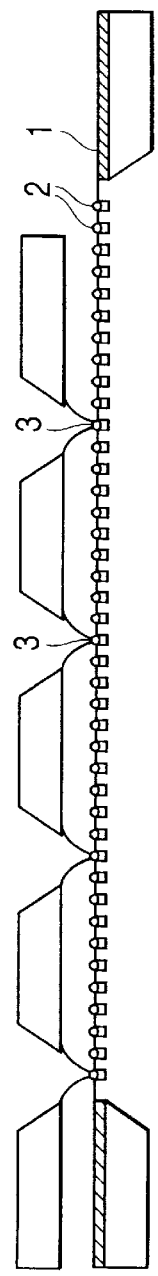

The present invention relates to a device and a process for the examination of cells using the patch-clamp method. Furthermore, the subject-matter of the present invention is the use of a, as such known, device for measuring bioelectric signals for examining cells.

STATE OF THE ART

The patch-clamp method is a process for measuring bio-electric signals, namely the electric potential inside a cell and the current created by ionic transport processes, the so-called ion channels, running through a cell membrane.

This process permits even measuring the current running through a cell membrane separately for a specific ion channel and in this manner to obtain information about how the cell membrane functions. Measurements with the patch-clamp method are conducted in neuroscience to investigate the effects of pharmaceuticals and chemotherapy on the action of the ion channels.

Devices for measuring bio-electric signals are known from DE 38 05 808 Al and U.S. Pat. Nos. 4,599,315, 5,229,163 and 5,643,742.

Various variants were developed from the patch-clamp method for determining the conductivity in individual membrane sections. For the examination, the membrane of a cell, usually a nerve cell, is suctioned with a glass capillary used as a micro-pipette and, depending on the variant, also penetrated in order to measure the intracellular potential of usually 1–500 $\mu$m V with an electrode located in the glass capillary compared to a reference electrode. The cell is mechanically firmly joined to the micro-pipette and is in contact with the surrounding solution via its membrane.

According to another variant, a suctioned part of a cell membrane is severed from the cell in order to then determine the conductivity of this piece of membrane (patch). With regard to the manner of membrane severance, there are various variants in common use for attaching the piece of membrane to the micro-pipette in both directions (inside-out patch or outside-out patch) for the subsequent measurements.

Measuring the potential inside the cell by measuring the currents through the cell membrane occurs with the aid of micro-electrodes which may be located inside the micro-pipette or be produced on substrates with known processes such as the thin-layer method. The to-be-examined neurons must be positioned on the substrates.

Although the patch-clamp method has become a state of the art measurement since its introduction in neuroscience, it is extremely sophisticated and hitherto requires microscopic control of the measure performed on the to-be-examined cell. A drawback is primarily that this process requires considerable skill and sensitivity of the operator for handling individual nerve cells. For instance, the neutrons have to be plated on a substrate and, if need be, also be positioned immediately at the micro-electrodes on the substrate surface in order to be able to carry out the necessary measurements.

Due to the manual handling of the individual cells, the patch-clamp method has hitherto involved considerable consumption of time. In particular, in the examination of a multiplicity of cells, this drawback is serious because the cells are spatially randomly distributed following their isolation from the tissue and for this reason can only be obtained, placed and examined in succession.

DESCRIPTION OF THE INVENTION

The present invention provides a device and a process with which a multiplicity of cells can be simultaneously examined using the patch clamp method, to automate cell examination in such a manner that microscope control is obviated. Furthermore, the examination of a multiplicity of cells on the smallest possible space should become possible and finally the time consumed for patch-clamp measuring is drastically minimized.

According to the present invention, the problems of the prior art are solved with a device having a plane arrangement of a first number of micro-cuvettes for receiving cells and having a plane arrangement of a second number of micro-pipettes which can be positioned relative to the plane arrangement of micro-cuvettes in order to simultaneously examine a multiplicity of cells located in the micro-cuvettes. Measuring the bio-electric signals occurs using the patch-damp method.

Furthermore, the problems of the prior art are solved according to the present invention by means of a process wherein a multiplicity of cells is arranged and a multiplicity of arranged cells is simultaneously examined by means of a multiplicity of micro-pipettes.

The systematic spatial arrangement of both the micro-cuvettes for the reception of the cells and the micro-pipettes permits for the first time automation of the patch-clamp method and thus conducting the patch-clamp method inexpensively and quickly. The to-be examined neurons are received by a plane arrangement of the micro-cuvettes, usually a substrate with uniformly distributed recesses in its surface, and in this manner retained in exactly determinable positions. With exact positioning, a plane arrangement of micro-pipettes in relation to the arrangement of the cells located in micro-cuvettes permits conducting a multiplicity of single measurements simultaneously, which hitherto could only be conducted successively and simultaneous observation with a microscope. The micro-pipettes relative to the micro-cuvettes can be arranged in an extremely confined space and permit in this manner the construction of very compact measuring devices. The cuvettes and pipettes are preferably uniformly distributed on the provided areas, i.e. with fixed spacing in relation to each other with the cuvettes and pipettes forming an uniform grid. In practice, the exact design of the grid will be dependent on the size and shape of the micro-pipettes and the micro-cuvettes.

A preferred embodiment of the device provides that the grid dimensions of a plane arrangement of the micro-cuvettes matches the plane arrangement of the micro-pipettes but is smaller in at least one direction and that the arrangement of micro-cuvettes and the arrangement of micro-pipettes can be laterally offset in relation to each other in order to repeatedly examine a multiplicity of cells simultaneously.

In a simplest case of an uniform arrangement, the distance between adjacent micro-cuvettes corresponds to an integral fraction of the distance to the micro-pipettes, which are larger than the micro-cuvettes. A substantially greater number of cells can be simultaneously received than is the case with an arrangement of an equal number of cuvettes as pipettes. The number of simultaneous measurements is only limited by the size of the micro-pipettes respectively and by the size of the areas provided for them. In order to examine all the cells located in the micro-cuvettes, the corresponding preferred embodiment of the process provides that the multiplicity of the micro-pipettes is offset relative to the cell arrangement and a multiplicity of arranged cells is repeatedly examined. In this manner, the multiplicity measurement is repeated in short intervals without needing to intermittently replace the cells, leading to an additional increase in the throughput.

Another embodiment of the present invention provides a micro-motor for positioning and/or for offsetting the arrangement of micro-cuvettes and the arrangement of micro-pipettes. The micro-motor for lowering the micro-pipette arrangement onto the micro-pipette arrangement and for lateral reciprocal movement ensures, with the aid of present day precision mechanics and micro-technology, pinpoint contacting of neurons and pipettes, thereby permitting with the present invention for the first time the examination of a multiplicity of cells.

The arrangement of the pipettes or the cuvettes can be moved by the micro-motor.

Another embodiment of the invention provides a cell feed device and or a rinsing device for removing the cells, which leads to further automation of the measurements and thereby to further saving of time, in particular, in the case of multiple measuring, which exceeds the reception capacity of the group of cuvettes.

Another embodiment of the invention provides a filter on the rear side of the arrangement of the micro-cuvettes. Rinsing the cuvette arrangement from the rear side is recommended, because the to-be-examined cells are introduced into the micro-cuvettes from the side facing the pipette arrangement and the micro-cuvettes are preferably widened conically in the direction of the pipettes. In this case, a filter is advantageous in order to prevent blockage of the micro-cuvette by the small particles.

DESCRIPTION OF THE INVENTION

The present invention is made more apparent in the following using preferred embodiments with reference to the accompanying drawings, to which reference is explicitly made with regard to the disclosure without the intention of limiting the scope or spirit of the overall invention.

Figure 2:
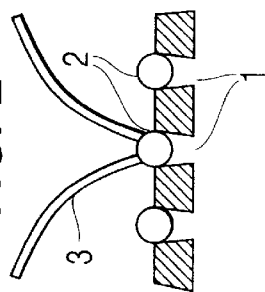
Figure 3:
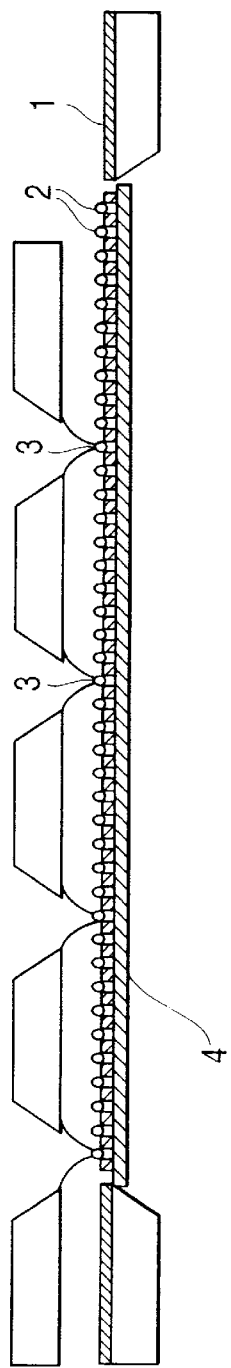
Figure 4:
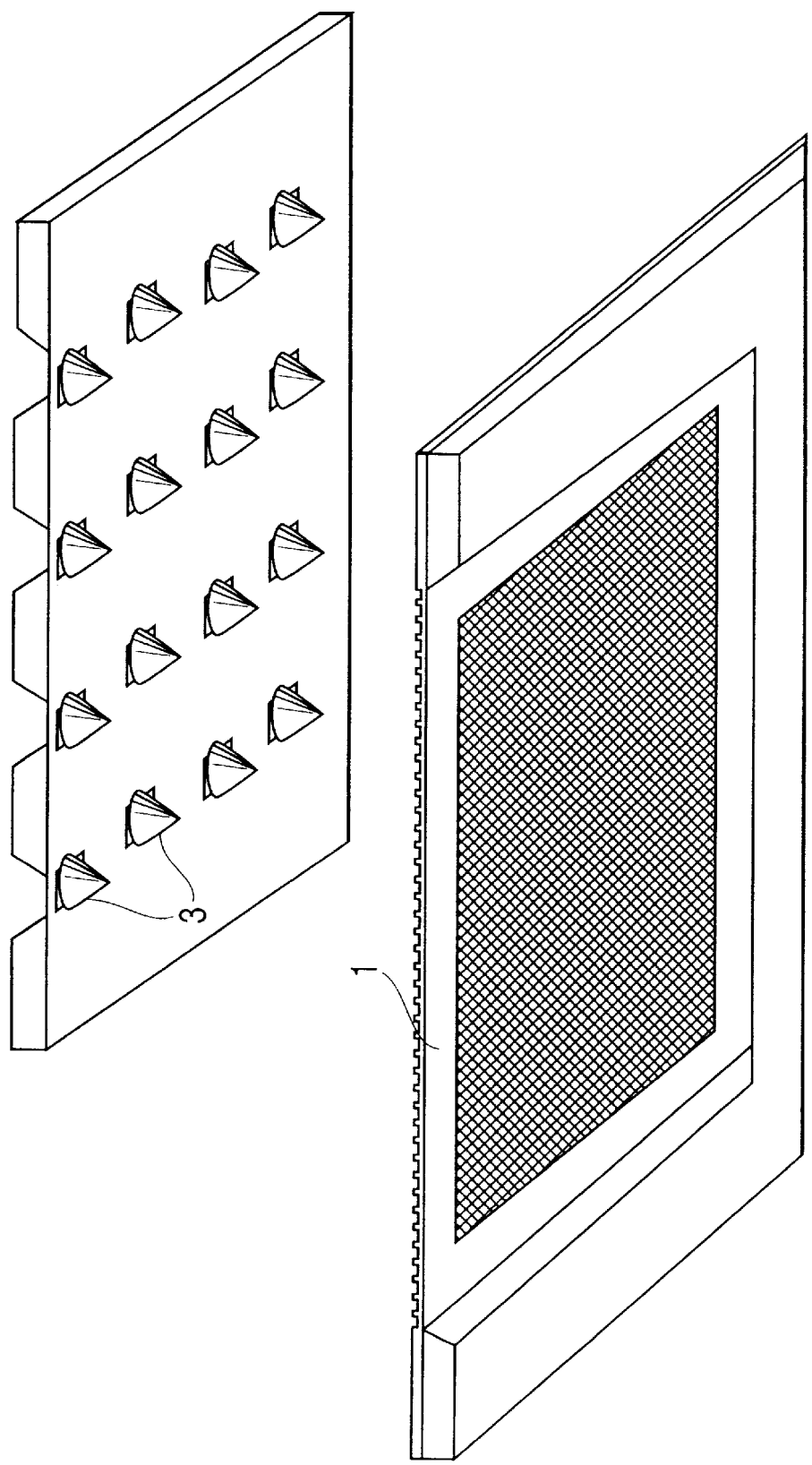

FIG. 1 is a cross section of a device during patch-clamp measuring according to the invention, FIG. 2 is an enlarged detail from FIG. 1, FIG. 3 is a cross section of a preferred embodiment of a device according to the invention, and FIG. 4 is an exploded view of arrangements of the microcuvettes and the micro-pipettes in accordance with the invention.

DESCRIPTION OF PREFERRED EMBODIMENTS OF THE INVENTION

FIGS. 1 and 2 show diagrams of a device during patch-clamp measurement in accordance with the invention. A micro-cuvettes arrangement 1 is provided with a multiplicity of micro-cuvettes for the reception of a multiplicity of cells 2 arranged in a grid. Some of the cells are touched by a micro-pipette arrangement 3 and respectively suctioned by the micro-pipettes. With this arrangement of n×n pipettes, $n^2$ measurements can be simultaneously conducted.

FIG. 3 shows a preferred embodiment of the device of the invention with a filter 4 located below the micro-cuvettes. Otherwise FIG. 3 is like FIG. 1.

FIG. 4 shows the spatial arrangement of the micro-cuvette arrangement (MKA) and of the micro-pipette arrangement (MPA). The MPA is located above the MKA, with the tapered openings of the micro-pipettes facing the MKA. The MPA can be moved relative to the MKA by a micro-motor (not illustrated).

The following dimensions are given by way of example for estimating approximately the typical dimensions of the device of the invention without the intention of limiting the scope or spirit of the invention.

For example, 160 cuvettes are located on an area of 8×8 $MM^2$ in each direction of the square grid on the micro-cuvettes arrangement the size of one square centimeter, thus 25,600 cuvettes are located at a mutual distance of 50 $\mu$m. The micro-pipette arrangement has 16 micro-pipettes (nozzles) spaced at a mutual distance 400 $\mu$m in a square grid on an area of at least 2×2 $mm^2$. The size of the grid of the micro-pipette arrangement corresponds, thus to the eight-fold grid size of the micro-cuvettes arrangement. In order to examine all the cells located in the MKA, the MPA can be-moved in parallel in both directions to the MKA in 40 steps and therefore be brought into all told 1600 different positions.

The MCA and MPA are produced with the aid of lithographic methods of semiconductor technology, the electrodes of the MPA being produced using thin-film technology.

Micro-mechanical structures serve to align the motor; the components are connected using precision mechanical and micro-technological means.

A micro-processor controls the micro-actors and gathers the measured data, which are electronically evaluated.

Currently, several thousand measurements can be conducted in a few minutes with the device and the process of the invention.

What is claimed is:

1. A device for examining cells comprising:

a plane arrangement of a first number micro-cuvettes for receiving cells; and a plane arrangement of a second number of micro-pipettes, which are movable in relation to the plane arrangement of micro-cuvettes to simultaneously position the micro-pipettes in registration with a multiplicity of cells located in the micro-cuvettes; and wherein the second number is greater than the first number.

2. A device in accordance with claim 1 wherein:

the second number is a product of a positive integer greater than one and the first number.

3. The device according to claim 1, wherein the plane arrangement of micro-cuvettes has grid dimensions matching the plane arrangement of micro-pipettes but the grid dimension are at least smaller in one direction and the arrangement of micro-cuvettes and the arrangement of pipettes are laterally offset in relation to each other with relative motion between the arrangement of micro-pipettes cuvettes and the arrangement of pipettes being used to examine a multiplicity of cells simultaneously.

4. The device according to claim 2, wherein the plane arrangement of micro-cuvettes has grid dimensions matching the plane arrangement of micro-pipettes but the grid dimensions are at least smaller in one direction, and the arrangement of micro-cuvettes and the arrangement of pipettes are laterally offset in relation to each other with relative motion between the arrangement of micro-cuvettes and the arrangement of pipettes being used to examine a multiplicity of cells simultaneously.

5. The device according to claim 1, comprising:
a motor for moving the arrangement of micro-cuvettes and the arrangement of micro-pipettes in relation to each other.
6. The device according to claim 2, comprising:
a motor for moving the arrangement of micro-cuvettes and the arrangement of micro-pipettes in relation to each other.
7. The device according to claim 3, comprising:
a motor for moving the arrangement of micro-cuvettes and the arrangement of micro-pipettes in relation to each other.
8. The device according to claim 4, comprising:
a motor for moving the arrangement of micro-cuvettes and the arrangement of micro-pipettes in relation to each other.
9. The device according to claim 1, comprising:
a cell feed device for feeding the cells to the micro-cuvettes.
10. The device according to claim 1 comprising:
a rinsing device for removing the cells.
11. The device according to claim 2, comprising:
a cell feed device for feeding the cells to the micro-cuvettes.
12. The device according to claim 2 comprising:
a rinsing device for removing the cells.
13. The device according to claim 3, comprising:
a cell feed device for feeding the cells to the micro-cuvettes.
14. The device according to claim 3 comprising:
a rinsing device for removing the cells.
15. The device according to claim 4, comprising:
a cell feed device for feeding the cells to the micro-cuvettes.
16. The device according to claim 4 comprising:
a rinsing device for removing the cells.
17. The device according to claim 5, comprising:
a cell feed device for feeding the cells to the micro-cuvettes.
18. The device according to claim 5 comprising:
a rinsing device for removing the cells.
19. The device according to claim 6, comprising:
a cell feed device for feeding the cells to the micro-cuvettes.
20. The device according to claim 6 comprising:
a rinsing device for removing the cells.
21. The device according to claim 7, comprising:
a cell feed device for feeding the cells to the micro-cuvettes.
22. The device according to claim 7 comprising:
a rinsing device for removing the cells.
23. The device according to claim 8, comprising:
a cell feed device for feeding the cells to the micro-cuvettes.
24. The device according to claim 8 comprising:
a rinsing device for removing the cells.
25. The device according to claim 2 comprising:
a filter on a rear side of the arrangement of micro-cuvettes.
26. The device according to claim 2 comprising:
a filter on a rear side of the arrangement of micro-cuvettes.
27. The device according to claim 3 comprising:
a filter on a rear side of the arrangement of micro-cuvettes.
28. The device according to claim 4 comprising:
a filter on a rear side of the arrangement of micro-cuvettes.
29. The device according to claim 5 comprising:
a filter on a rear side of the arrangement of micro-cuvettes.
30. The device according to claim 6 comprising:
a filter on a rear side of the arrangement of micro-cuvettes.
31. The device according to claim 7 comprising:
a filter on a rear side of the arrangement of micro-cuvettes.
32. The device according to claim 8 comprising:
a filter on a rear side of the arrangement of micro-cuvettes.
33. A process for examining cells comprising:
providing a multiplicity of cells which are examined simultaneously using micro-pipettes and the patch-clamp method.
34. The process according to claim 33 wherein:
the micro-pipettes and an arrangement of cells are offset in relation to each other and different cells are sequentially suctioned into the micro-pipettes from an array of micro-cuvettes.
35. A device in accordance with claim 1 wherein:
the device uses the patch-clamp method.

* * * * *